(12) United States Patent
Blume

(10) Patent No.: US 9,161,921 B2
(45) Date of Patent: Oct. 20, 2015

(54) COLLOIDAL CARRIER SYSTEM WITH PENETRATION PROPERTIES FOR ENCAPSULATING LIPOPHILIC ACTIVE AGENTS AND OILS FOR TOPICAL USE

(76) Inventor: Gabriele Blume, Steinau an der Strasse (DE)

( * ) Notice: Subject to any disclaimer, the term of this patent is extended or adjusted under 35 U.S.C. 154(b) by 148 days.

(21) Appl. No.: 13/977,097

(22) PCT Filed: Nov. 24, 2011

(86) PCT No.: PCT/DE2011/002026
§ 371 (c)(1),
(2), (4) Date: Jun. 28, 2013

(87) PCT Pub. No.: WO2012/089184
PCT Pub. Date: Jul. 5, 2012

(65) Prior Publication Data
US 2013/0273123 A1    Oct. 17, 2013

(30) Foreign Application Priority Data
Dec. 28, 2010    (DE) .......................... 10 2010 056 192

(51) Int. Cl.
| | |
|---|---|
| *A61K 9/51* | (2006.01) |
| *A61K 8/11* | (2006.01) |
| *A61K 8/37* | (2006.01) |
| *A61K 8/67* | (2006.01) |
| *A61K 8/92* | (2006.01) |
| *A61Q 19/00* | (2006.01) |
| *A61Q 19/08* | (2006.01) |

(52) U.S. Cl.
CPC ... *A61K 9/51* (2013.01); *A61K 8/11* (2013.01); *A61K 8/375* (2013.01); *A61K 8/671* (2013.01); *A61K 8/678* (2013.01); *A61K 8/925* (2013.01); *A61Q 19/00* (2013.01); *A61Q 19/08* (2013.01); *A61K 2800/413* (2013.01)

(58) Field of Classification Search
CPC ......... A61K 8/11; A61K 8/375; A61K 8/671; A61K 9/51
USPC ........................................................ 424/400
See application file for complete search history.

(56) References Cited

U.S. PATENT DOCUMENTS

| | | | |
|---|---|---|---|
| 5,753,241 A | 5/1998 | Ribier et al. | |
| 6,274,150 B1 | 8/2001 | Simonnet et al. | |
| 6,335,022 B1 | 1/2002 | Simonnet et al. | |
| 6,375,960 B1 | 4/2002 | Simonnet et al. | |
| 6,413,527 B1 | 7/2002 | Simonnet et al. | |
| 6,419,946 B1 | 7/2002 | Sonneville et al. | |
| 6,541,018 B1 | 4/2003 | Simonnet et al. | |
| 6,689,371 B1 | 2/2004 | Simonnet et al. | |
| 6,902,737 B2 | 6/2005 | Quemin | |
| 2008/0193393 A1 | 8/2008 | Dayan | |
| 2009/0208541 A1 | 8/2009 | Gesztesi et al. | |
| 2009/0324727 A1 | 12/2009 | Foguet Roca | |

FOREIGN PATENT DOCUMENTS

| | | |
|---|---|---|
| CN | 101869539 A | 10/2010 |
| DE | 100 54 919 A1 | 5/2002 |
| EP | 0 728 460 B1 | 8/1997 |
| EP | 1 020 219 B1 | 3/2001 |
| EP | 1 010 414 B1 | 4/2001 |
| EP | 1 016 453 B1 | 9/2001 |
| EP | 1 010 416 B1 | 10/2001 |
| EP | 1 013 338 B1 | 10/2001 |
| EP | 1 010 415 B1 | 1/2002 |
| EP | 1 025 898 B1 | 1/2002 |
| EP | 1 010 413 B1 | 11/2002 |
| EP | 1 353 629 B1 | 2/2006 |
| EP | 1 839 644 A2 | 10/2007 |
| WO | 2006/087156 | 8/2006 |

OTHER PUBLICATIONS

Sasol; Title: Excipients for pharmaceuticals, published Jul. 2010, obtained from online address www.sasol.com.*
The International Search Report as mailed on May 13, 2013 for International Application No. PCT/DE2011/002026.
Justas Barauskas, et al., "'Sponge' Nanoparticle Dispersions in Aqueous Mixtures of Diglycerol Monooleate, Glycerol Dioleate, and Polysorbate 80," Langmuir, Bd. 22, Nr. 14, Jul. 1, 2006, pp. 6328-6334, XP055059935.
Database WPI, Thomas Scientific, London, GB; XP002695563, "Composite nanoemulsion for recovering and desensitizing sensitive skin, comprises isopropyl myristate, polyglyceryl-3-oleate, distilled water, citric acid, sodium citrate, metallothionein, Chrysanthemum extract, oxymatrine and vitamin E," Oct. 27, 2010.
Wikipedia, "Okklusion (Pharmazie)," pp. 1-3; English translation from German to English.
Sebastian Jager, et al., "Pharmacology of Selected Terpens," Pharmazeutische Zeitung, 2012.
PCT English Translation of the International Preliminary Report on Patentability, PCT/DE2011/002026, Aug. 22, 2013, 10 pages.

* cited by examiner

*Primary Examiner* — Johann R Richter
*Assistant Examiner* — Yanzhi Zhang
(74) *Attorney, Agent, or Firm* — Quarles & Brady, LLP

(57) ABSTRACT

The invention relates to a colloidal carrier system in the form of a nanocapsule, comprising at least the following components: a liquid lipid core, a continuous shell surrounding the core, containing at least one membrane-forming, natural anionic emulsifier and at least one single-chain, natural non-ionic co-emulsifier selected from the group of diglyceryl-monooleates, diglyceryl-monolinoleates, polyglyceryl-monooleates, polyglyceryl-monolinoleates.

17 Claims, 1 Drawing Sheet

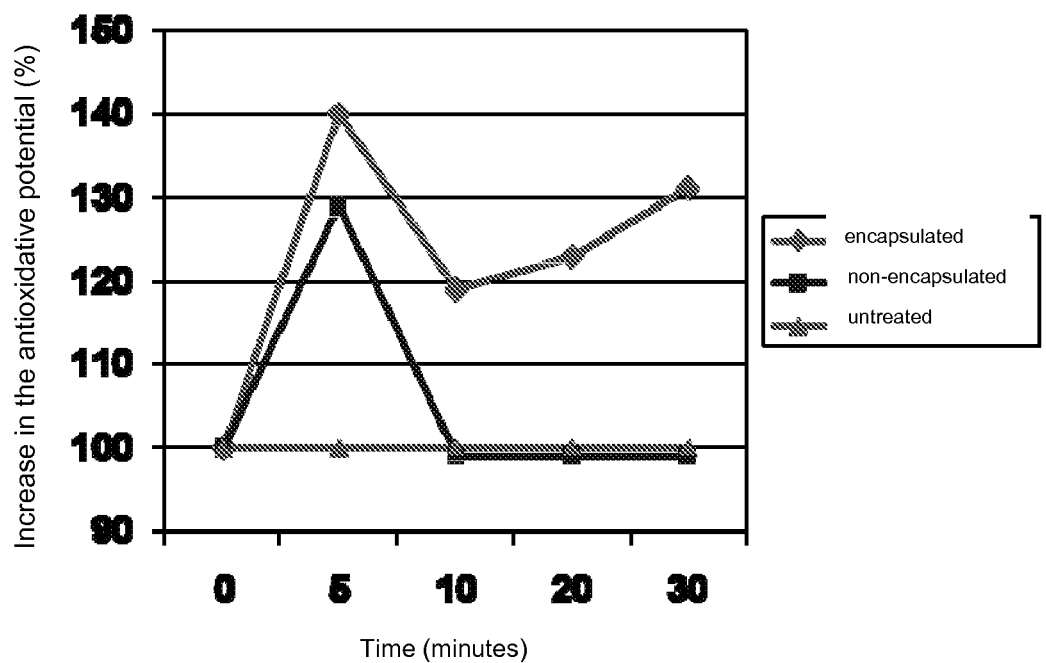

COLLOIDAL CARRIER SYSTEM WITH PENETRATION PROPERTIES FOR ENCAPSULATING LIPOPHILIC ACTIVE AGENTS AND OILS FOR TOPICAL USE

CROSS-REFERENCE TO RELATED APPLICATIONS

This application represents the national stage entry of PCT International Application No. PCT/DE2011/002026 on Nov. 24, 2011 and claims the benefit of German Patent Application No. 10 2010 056 192.4 filed Dec. 28, 2010. The contents of these applications are hereby incorporated by reference as if set forth in their entirety herein.

The invention relates to the encapsulation of lipophilic agents of low solubility and oils in the form of a colloidal system (droplets).

The encapsulation of lipophilic agents in particles with a size in the sub-micrometer range—oil-in-water nanoemulsions, respectively microemulsions—has been known for many years. Emulsions of this sort are commonly used in particular in cosmetics and dermatology.

Microemulsions differ from classic emulsions in terms of their very small droplet size between 10 and <100 nm. Visible light cannot be scattered by them, which makes the microemulsions appear transparent like water.

For example, in patent application DE 100 54 919 (A1), a microemulsion with a droplet size of about 20 nm is described, which for encapsulating the lipophilic phase (40% wt.-%) requires a mixture of a surfactant (Tween 80=polyoxyethylene-20-sorbitan-monooleate) and co-surfactant (poloxamer 311) in an amount of up to 30 wt.-%. The microemulsion allows the transport of the encapsulated agent (here: Lidocaine) into the skin.

A further description of a microemulsion (US 2009/0324727 A1) is also based on the surfactant Tween 80, and this time lecithin is used as a co-emulsifier. Here, too, a high amount of emulsifier (up to 30%) is required for encapsulating the oil (15%) with the addition of a polyvalent alcohol.

From a dermatological point of view, the oftentimes rather high surfactant content of the microemulsions is to be rated as disadvantageous since it poses the risk of skin irritations occurring and causes a sticky sensation when applied to the skin. Additionally, the formulation range of said microemulsions is generally very limited (application predominantly as a spray emulsion or aqueous gel).

Nanoemulsions (particle size 50-250 nm) are meta-stable oil-in-water emulsions in which a lipophilic—usually liquid—core is surrounded by a shell of amphiphilic, surface active molecules. These emulsions are used in cosmetics and pharmaceutics predominantly for solubilizing in water the lipophilic components of low solubility and for their stabilization. Nanoemulsions—to some extent also transparent ones—with small droplet sizes can only be produced by means of a high pressure homogenizer.

In its patents EP 728 460 (B1) and EP 1 353 629 (B1), L'Oreal describes transparent nanoemulsions with a droplet size of <100 nm based on liquid, non-ionic, amphiphilic, surface active substances. These non-ionic surfactants belong to the group of the polyoxyethylene glycol esters ($PEG_n$ esters). In the following two documents, too, this type of emulsifier is used as a component for the formation of the shell of nanoemulsions (EP 1 839 644 A2 and US 2009/0208541 A1). However, none of the just cited documents describes the transport of lipophilic agents into the deeper layers of the skin by means of the colloidal particles.

With its product "Tinoderm E", the company Ciba has put on the market a transparent nanoemulsion which with its particle size of 20-40 nm allows vitamin E situated in the oil core to be transported into the skin. The penetration properties are attributed to the very small particle size, which corresponds to the smallest intermediate distances in the upper skin layers. Here, too, the emulsifier mixture for producing the nanoemulsion comprises a polyoxyethylene glycol ester.

In cosmetics, however, the trend is towards PEG-free (polyoxyethylene glycol-free) formulations, which is why nanoemulsions with natural, herbal emulsifiers are to be produced where possible.

In a plurality of patents, the company L'Oreal describes "nanoemulsions based on a surface active substance and at least one oil with a molar mass above 400, wherein the weight ratio of the amount of oil to the amount of surface active substance is between 2 and 10. The size of the oil globules is very small and ranges below 100 nm, usually in the range of 40 to 60 nm.

In EP 1 010 413 (B1) the surface active substances are: sugar fatty acid esters or sugar fatty alcohol ethers; in EP 1 010 414 (B1) the surface active substances are: mixed esters of fatty acids or alcohol, of carboxylic acids and glyceryl; in EP 1 010 415 (B1) the surface active substances are: fatty acid esters of ethoxylated or non-ethoxylated sorbitan; in EP 1 010 416 (B1) the surface active substances are: fatty acid esters of glycerin; in EP 1 013 338 (B1) the surface active substances are: fatty acid esters of phosphoric acid; in EP 1 016 453 the surface active ingredients are: ethoxylated fatty alcohol ethers or ethoxylated fatty acid esters; in EP 1 020 219 the surface active substances are: alkyl ether citrate, and in patent EP 1 025 898, the surface active substances are: alkoxylated alkenyl succinates and alkoxylated alkenyl succinates of glucose.

All these patents are based on the same application example—a fluid for make-up removal—with always the same composition and the same weight amounts; only the one emulsifier (surface active substance) varies.

In all the above-mentioned patents, no information is given as to the transport of the agents potentially encapsulated in the droplets into the skin and as to their bioavailability in the epidermis.

The transport of actives into the skin with the help of a colloidal carrier system (size between 100 and 200 nm) is described only in the American patent application US 2008/0193393. The carrier system is based on an oil core which contains the dissolved lipophilic agent and is surrounded by a membrane of phospholipids and fatty acids. However, it must be stressed here that, in the penetration tests, the formulation was applied occlusively (by using Parafilm), which does not correspond to reality. Occlusion leads to an accumulation of moisture in the horny layers of the skin (*stratum corneum*), which results in swelling. The increased amount of available water facilitates the penetration of a large portion of pharmaceutical agents (active agent penetration) (Wikipedia).

Thus, the object arose to provide a penetrating colloidal carrier system enabling an increased encapsulation of lipophilic agents which can be produced in a simple manner.

This object is attained by the colloidal carrier system according to the invention, which comprises the following components:
  a liquid lipid core
  a continuous shell surrounding the core, said shell being formed from an anionic, membrane-forming emulsifier and at least one non-ionic single-chain co-emulsifier, selected from the group of diglyceryl-monooleates, diglyceryl-monolinoleates, polyglyceryl-monooleates, polyglyceryl-monolinoleates.

The object is further attained by a preparation comprising the colloidal carrier system as described in the following.

The carrier system according to the invention is present in an aqueous dispersion so that the enclosed lipophilic agents in higher concentrations can be incorporated easily into water-based formulations, such as spray formulations, gels or lotions and O/W emulsions. It is to be noted, particularly, that these particles allow the enclosed agents to penetrate into the skin and, thus, function as a colloidal agent carrier system.

Further, the colloidal system stabilizes enclosed sensitive molecules, such as vitamins, against degradation. The combination of a membrane-forming anionic natural emulsifier with a co-emulsifier (stabilizer) as mentioned in claim 1 leads to a high degree of encapsulation of lipophilic agents in the aqueous medium.

The colloidal carrier system according to the invention has a negative charge and preferably a size of 100 to 200 nm. A colloidal carrier system of this sort, having a droplet size of 100 to 200 nm, which allows a transport of the encapsulated lipophilic components into the epidermis, is not known from the state of the art.

In a preferred embodiment, the preparation according to the invention further comprises a stabilizer (e.g. water-soluble alcohol or polyol) and can therefore be considered free of preservatives.

The aqueous preparation comprising the colloidal carrier system can itself be used as a cosmetic/pharmaceutical product, depending on the agent encapsulated. Furthermore, the aqueous preparation comprising the colloidal carrier system can be incorporated into the aqueous phase of another preparation, such as an emulsion, lotion, cream or different forms of gels, or it can itself be used, diluted with an added thickener, as a spray formulation.

The lipophilic substances of the present invention have a high encapsulating efficiency. The preparation according to the invention comprises the liquid lipid core advantageously in an amount of 15-40 wt.-%, preferably of 20-35 wt.-% based on the total amount of the preparation.

Further advantages of the preparation according to the invention are the high stability of the preparation against phase separation, a pleasant skin feeling and the easy spreadability on the skin.

Apart from the membrane-forming herbal anionic emulsifier (forming lamellar structures), another herbal, non-ionic single-chain co-emulsifier is employed, both comprising long-chain fatty acids (e.g. palmitic acid, stearic acid, oleic acid and/or linoleic acid) as the hydrophobic component.

These emulsifiers with a long alkyl chain are characterized by a high skin tolerance and can achieve cosmetic and pharmaceutical effects (e.g. increase in skin smoothness, reduction of metalloproteases, reduction of skin blemishes).

Preferably, glyceryl citrate/lactate/linoleate/oleate (Imwitor 375), respectively glyceryl citrate/lactate/stearate from the company Sasol are used as emulsifiers for forming the capsule shell.

As co-emulsifiers, diglyceryl-monooleates are preferably used.

The amount of the membrane-forming emulsifier glyceryl citrate/lactate/linoleate/oleate (Imwitor 375) in the preparations according to the invention ranges between 3 and 6 wt.-% and the amount of co-emulsifier (e.g. diglyceryl-monooleate Nikkol DGMO) ranges between 1 and 3 wt.-%. Both components form the shell which surrounds the liquid lipid core.

The oil core preferably comprises natural herbal oils and lipophilic agents dissolved in it. The oil core preferably constitutes between 20 and 35% based on to the entire formulation, and the membrane-forming components constitute between 4 and 8%.

Fatty substances are preferably understood to be natural and synthetic cosmetic oil components and natural and synthetic waxes, which according to the invention are liquid at room temperature. These oil components are physiologically acceptable and skin-friendly.

The fatty substance can in particular be a non-polar or polar liquid oil, which can be natural or synthetic. The oil component can in particular be selected from natural oils, in particular sunflower oil, olive oil, soya oil, rapeseed oil, almond oil, orange oil, wheat germ oil, peach oil, sesame oil, avocado oil, babassu oil, rosehip oil, evening primrose oil and the liquid components of the coconut oil. However, other triglyceride oils are suitable as well, such as synthetic triglyceride oils, liquid paraffin oils from synthetic hydrocarbons as well as from volatile and non-volatile silicone oils.

Further, difatty and trifatty acid esters, in particular trifatty acid esters, of saturated and/or unsaturated linear and/or branched fatty acids, in particular $C_6$-$C_{22}$ fatty acids, with glycerin, such as triglycerides of capric acid and/or caprylic acids such as neutral oil, respectively triglycerides from conjugated linoleic acid (CLA) such as Clarinol G-80 by Lipid Nutrition, can be employed.

As natural or synthetic waxes, liquid plant waxes such as jojoba wax can be used according to the invention.

According to the invention, any given combination of the above-named fatty substances can be used.

These oils can also serve on their own as cosmetic/pharmaceutical raw materials.

In one embodiment particularly preferred according to the invention, the nanocapsules contain natural herbal oil which is selected according to its physiological function, e.g.: apricot oil or olive oil for dry skin or evening primrose oil for sensitive skin.

The oils and liquid fatty substances also serve as solvents for hydrophobic agents, such as retinol in sunflower oil.

The preparation according to the invention can comprise one and/or more lipophilic actives. All substances which can be dissolved in oil at room temperature or in heat and which have cosmetically and/or pharmaceutically relevant effects in or on the skin are to be considered as lipophilic actives of this sort. Preferably, these active ingredients are of natural origin, particularly preferably of herbal origin. An extract of the usable cosmetically and/or dermatologically effective lipophilic substances can consist of: algae and plant extracts (e.g. Phlorogine by Biotechmarine, an algae extract for treating oily skin or e.g.: Incromega V3 by Croda, a plant extract from Echiomega); anti-cellulite active substances (e.g. CLA); anti-elastase and anti-collagenase active substances (e.g. unsaturated fatty acids such as oleic acid or EPA); anti-inflammatory active substances (e.g. EPA=eicosapentaenoic acid); antioxidants (e.g. salvia extract by Flavex, lipoic acid and its derivatives); ceramides (e.g. different ceramides by the company Cosmoferm); skin-calming and skin-smoothing agents (e.g. bisabolol); moisturizers (e.g. glycerol monoisostearates, sucrose polysoyates); flavonoids (flavanols, flavanones, anthocyanidines, flavones and flavonoles, such as sinensetin, or polyphenols such as the ones in green tea or grapes belong to the flavonoids); phytosterols (such as β-sitostreol from corn fiber oil); radical scavengers (e.g. ubiquinol derivatives such as co-enzyme Q10); saponins (e.g. from ginseng, liquorice root and horse chestnut); oxygen-binding substances (e.g. perfluorodecaline); sebum-reducing substances (e.g. 10-hydroxydecanoic acid); substances which promote blood circulation and thus the care of the skin (e.g. nicotinic acid ester); terpenes (cosmetically and dermatologically relevant terpenes are listed in the *Pharmazeutische Zeitung*, Magazine No. 22; 2006 by Sebastian Jager et al.); vitamins (retinol and derivatives, vitamin E and derivatives such as tocotrienols or carotenes and carotenoids, such as lycopenes, lutein or fucoxanthin, vitamin D and derivatives).

All these agents have the purpose of preventing, respectively inhibiting skin ageing and/or photoageing (due to UV radiation and environmental stress); of stimulating the synthesis of dermal and epidermal macromolecules or preventing their degradation; of promoting the proliferation of fibroblasts and keratinocytes and thus protecting and maintaining a healthy skin.

The cosmetic or pharmaceutical preparation according to the invention for skin protection can also comprise other components than the aforementioned ones. In a preferred embodiment, it comprises at least one of the listed substances. It can also comprise any given combination of the components listed under agents and oils.

The preparations according to the invention can further comprise at least one stabilizer, which preferably is an alcohol soluble in water. The stabilizer/solvent is preferably used in a concentration of 10-20 wt.-% based on the entire preparation. Depending on their pharmaceutical form, monovalent alcohols, such as ethanol, propanol or isopropanol, are suitable. Further, polyols soluble in water are suitable. They include diols, triols, and polyalcohols. $C_2$ to $C_{10}$ diols, in particular 1,2-propylene glycol, 1,2-butylene glycol, 1,3-butylene glycol and 1,4-butylene glycol, 1,2-pentanediol, 1,6-hexanediol and 1,2-octanediol are suitable among the diols. Further, glycerin and in particular diglycerin and triglycerin, 1,2,6-hexanetriol and dipropylene glycols are preferably suitable. For the production of the nanocapsules according to the invention, ethanol or 1,2-pentanediol (Hydrolite 5 by Symrise) are preferably used, in concentrations of 10 to 30 wt.-%, particularly preferably of 15-20 wt.-%, based on the entire formulation so that thus no other preservation (classic preservatives) is necessary. The preparation according to the invention can therefore be declared free of preservatives.

The invention described here also comprises the colloidal carrier system in cosmetically and dermatologically interesting aqueous formulations (spray formulations, various gels, lotions and creams) as well as their use for treating, protecting and caring for skin, hair, nails and lips.

In the following, the method for producing a preparation according to the invention is to be demonstrated with the help of several embodiments and illustrations which are not to be understood as limiting.

EXAMPLE 1

Colloidal Carrier System with Vitamin E and Fish Oil Against Psoriasis a) 1.4 g Imwitor 375 and 0.6 g diglyceryl-monooleates are dissolved under heat in 6 g ethanol.
b) 0.05 g Lipochroman-6 (antioxidant by Lipotec) are dissolved in 2 g ethanol. Then, 5 g fish oil (EPA from the company Croda, rich in omega-3 acids) and 5 g Tocopherol (vitamin E from the company BASF) are added. Add emulsifier to the oil phase.
c) Provide aqueous phase (29.95 g) and add oil phase while homogenizing,
then perform high pressure homogenization for 5 minutes at 800 bar.

This yields vesicles having a negative charge (−48 mV) and a particle size of 108 nm.

The stability of the oil phase was tested by storing the non-encapsulated oil and the encapsulated oil over 3 days at 40 degrees and measuring the activity of the antioxidants.

Over this period, the pure oil loses 29% of its activity whereas there was no reduction in activity if the oil was present encapsulated in the colloidal carrier system.

The carrier system is extremely stable. Thus, there is no solubilization of the droplets when adding 50% ethanol.

A measurement of the penetration of the non-encapsulated antioxidants (vitamin E and Lipochroman) dissolved in the oil versus encapsulation in the colloidal carrier system into the skin was determined with the help of ESR spectroscopy. The skin has natural antioxidative protection provided by natural enzymatic and non-enzymatic skin agents. This Skin Antioxidative Potential (SAP) can be measured by incubating the epidermis with test radicals and observing by ESR the reduction of the radicals after the antioxidants have penetrated into the skin. Topically applied antioxidants which can penetrate into the skin can then increase the SAP. While the non-encapsulated antioxidants can penetrate into the skin very quickly, they are also consumed within the skin very quickly and after 10 minutes the initial state is restored. The nanoemulsion shows an increase in the SAP, which is significantly higher already after 5 minutes, then it shows a slight drop and then again a rise. Over the entire tested period, a significant increase in the antioxidative capacity in the epidermis takes place, which can only be explained by a penetration of the antioxidants with the help of the colloidal carrier system. (FIG. 1)

Nanoemulsion Comprising Retinol Against Skin Ageing
a) Dissolve 0.1 g Lipochroman-6 (antioxidant from the company Lipotec) in 2 g ethanol and then add 33.3 g retinol 15S (15% retinol dissolved in sunflower oil by BASF)
b) dissolve 3.5 g Imwitor 375 and 1.5 g diglyceryl-monooleate in 14 g ethanol, merge phase a and phase b
c) provide 45.6 g water and add an oil phase while homogenizing, then perform high pressure homogenization for 5 minutes at 800 bar.

The resulting retinol nanocapsules with an agent content of 5% pure retinol have a particle size of 170 nm and carry a negative surface charge.

The invention claimed is:

1. A colloidal carrier system in the form of a nanocapsule, comprising at least the following components:
    a liquid lipid core, and
    a continuous shell surrounding the core comprising at least one membrane-forming, natural anionic emulsifier and at least one single-chain, natural non ionic co-emulsifier selected from the group consisting of diglyceryl-monooleates, diglyceryl-monolinoleates, polyglyceryl-monooleates, and polyglyceryl-monolinoleates, wherein the ratio of the emulsifier and co-emulsifier to the liquid lipid core is between 1:3 and 1:8;
    wherein the membrane-forming, natural anionic emulsifier is glyceryl/citrate/lactate/linoleate/oleate.

2. The colloidal carrier system according to claim 1, wherein the nanocapsule having a particle size of 100 to 200 nm.

3. The colloidal carrier system according to claim 1, wherein the single-chain, natural non-ionic co-emulsifier is diglyceryl-monooleates.

4. The colloidal carrier system according to claim 1, wherein the liquid lipid core is formed from
    one or more oil components and/or
    lipophilic agents which are dissolved in one or more oils.

5. A preparation comprising nanocapsules according to claim 1, which comprises the liquid lipid core in an amount of 20-35% and the membrane-forming emulsifiers and co-emulsifiers in an amount of 4-8% based on the total amount of the preparation, respectively.

6. The preparation according to claim 5, wherein the preparation is aqueous.

7. The preparation according to claim 5, which further comprises at least one stabilizer.

8. The preparation according to claim 5 for therapeutically treating the human or animal body.

9. The colloidal carrier system according to claim 2, wherein the membrane-forming natural anionic emulsifier is glyceryl/citrate/lactate/linoleate/oleate.

10. The colloidal carrier system according to claim 2, wherein the single-chain, natural non-ionic co-emulsifier is diglyceryl-monooleates.

11. The colloidal carrier system according to claim 2, wherein the liquid lipid core is formed from
one or more oil components and/or
lipophilic agents which are dissolved in one or more oils.

12. The colloidal carrier system according to claim 3, wherein the liquid lipid core is formed from
one or more oil components and/or
lipophilic agents which are dissolved in one or more oils.

13. The preparation comprising nanocapsules according to claim 2, which comprises the liquid lipid core in an amount of 20-35% and the membrane-forming emulsifiers and co-emulsifiers in an amount of 4-8% based on the total amount of the preparation, respectively.

14. The preparation comprising nanocapsules according to claim 3, which comprises the liquid lipid core in an amount of 20-35% and the membrane-forming emulsifiers and co-emulsifiers in an amount of 4-8% based on the total amount of the preparation, respectively.

15. The preparation comprising nanocapsules according to claim 4, which comprises the liquid lipid core in an amount of 20-35% and the membrane-forming emulsifiers and co-emulsifiers in an amount of 4-8% based on the total amount of the preparation, respectively.

16. The preparation according to claim 6, which further comprises at least one stabilizer.

17. A colloidal carrier system in the form of a nanocapsule, comprising at least the following components:
a liquid lipid core, and
a continuous shell surrounding the core comprising at least one membrane-forming, natural anionic emulsifier and at least one single-chain, natural non ionic co-emulsifier selected from the group consisting of diglyceryl-monooleates, diglyceryl-monolinoleates, polyglyceryl-monooleates, and polyglyceryl-monolinoleates,
wherein the liquid lipid core contains natural herbal oils and lipophilic agents dissolved therein,
wherein the oil constitutes between 20% and 35% based on the entire formulation, and
wherein the membrane-forming components constitute between 4% and 8%.

* * * * *

UNITED STATES PATENT AND TRADEMARK OFFICE
CERTIFICATE OF CORRECTION

Page 1 of 1

PATENT NO.       : 9,161,921 B2
APPLICATION NO.  : 13/977097
DATED            : October 20, 2015
INVENTOR(S)      : Gabriele Blume It is certified that error appears in the above-identified patent and that said Letters Patent is hereby corrected as shown below:

In the claims

Column 8, line 25   -   "wherein the oil constitutes between 20% and 35% based on" should be "wherein the oil core constitutes between 20% and 35% based on"

Signed and Sealed this
Fifth Day of April, 2016

Michelle K. Lee
*Director of the United States Patent and Trademark Office*